(12) United States Patent
Yasuda et al.

(10) Patent No.: US 6,346,982 B1
(45) Date of Patent: Feb. 12, 2002

(54) DEVICE FOR EXAMINING FLAT WORKPIECES

(75) Inventors: Nobuyuki Yasuda; Masatoshi Yasuda, both of Osaka (JP)

(73) Assignee: Kabushiki Kaisha Yutaka, Osaka (JP)

( * ) Notice: Subject to any disclaimer, the term of this patent is extended or adjusted under 35 U.S.C. 154(b) by 0 days.

(21) Appl. No.: 09/514,341

(22) Filed: Feb. 28, 2000

(30) Foreign Application Priority Data

Jun. 4, 1999 (JP) .......................................... 11-158267

(51) Int. Cl.[7] .............................................. G01N 21/00
(52) U.S. Cl. .................................. 356/237.1; 356/237.2
(58) Field of Search .......................... 356/237.1, 239.1, 356/239.2, 239.3, 239.7, 239.8, 240.1, 237.2, 237.3, 237.4, 237.5; 250/221, 222.1, 222.2, 223 R, 559.01, 559.07, 559.08

(56) References Cited

U.S. PATENT DOCUMENTS

| | | | | |
|---|---|---|---|---|
| 4,492,475 A | * | 1/1985 | Takahashi | .................... 356/427 |
| 5,136,157 A | * | 8/1992 | Apter et al. | ............ 250/223 B |
| 5,404,227 A | * | 4/1995 | Sumita et al. | ............... 356/428 |

* cited by examiner

Primary Examiner—Frank G. Font
Assistant Examiner—Michael P. Stafira
(74) Attorney, Agent, or Firm—Wenderoth, Lind & Ponack, L.L.P.

(57) ABSTRACT

A device which can examine flat workpieces such as coins to distinguish them between defectives and nondefectives with high accurancy in a production line. Workpieces carried on a belt conveyor are moved onto a turntable formed from a transparent hard material for examination. For examination, each workpiece is photographer by a camera while shedding light on the workpiece from a strobe provide opposite the camera with the turntable therebetween.

5 Claims, 5 Drawing Sheets

DEVICE FOR EXAMINING FLAT WORKPIECES

BACKGROUND OF THE INVENTION

The invention relates to a device for distinguishing good from bad among flat small workpieces, and more particularly a device capable of high-precision inline inspection of coins formed e.g. by a press.

High accuracy is sometimes required for thin, flat, small workpieces formed by continuously blanking a sheet material in a press. To remove defective workpieces, it is necessary to examine each workpiece for its dimension, chipping of the edge, and position of holes or slits if any.

An image sensor (or image processor) is considered to be the best choice for such examination. A typical such image sensor includes a high-definition CCD camera for photographing each workpiece, and a control unit for subjecting the photos taken to binarizing and density adjustment and operation to determine if each workpiece is up to standard. This sensor is used for examination on whether or not necessary parts are actually mounted, and for size, directional, dimensional, positional and other examinations. Newest image sensors even have sub-pixel processing functions, i.e. the function of processing images on the order of 0.1 pixel, and the function of counting the number of edges. Such sensors increase the reliability of examination.

Some workpieces formed by blanking in a press sometimes require certain post-treatment. For example, on a press, a small amount of oil is applied to a mold of a press to extend the life of the mold and to improve releasability. In such a case, it is necessary to remove oil from workpieces formed by the press by washing and then to dry them. It is desired to pick out and eliminate any defective workpieces before such post-treatment to save time, cost and energy.

Finding defective workpieces as soon as possible is also important in finding any failure situation of the press. For example, from the fact that defective workpieces are found continuously, one can know that the mold of the press has been worn or otherwise damaged.

For this reason, inline examination of workpieces immediately after they are formed by pressing is extremely effective. But actually, it is difficult to examine workpieces while being carried on a belt conveyor from the press with high reliability.

Flat small workpieces are laid flat on the belt conveyor, and are photographed by an overhead camera while shedding light from above (reflection lighting) for examination by an image sensor.

One problem of such a reflection lighting system is that the camera cannot distinguish soiling, scratches and foreign matter on the conveyor from deficiencies of workpieces.

The degree of soiling of the conveyor varies with the number of workpieces processed and the degree of oil adhered. But the camera usually tends to pick up noises (on the images) in less than several hours.

If the belt conveyor is made of a soft material such as polyurethane, foreign objects such as powdery metal pieces tend to stick on the belt surface. Once stuck, they are not easily removable by e.g. a scraper. The number of such foreign objects and scratches on the belt surface tends to increase with time, and they appear as noises in the photos taken by the camera. When such noises increases to a certain level, no accurate examination is possible any longer.

When workpieces are formed by blanking on a press, they are blanked from a front side of the sheet to its back side. Thus, the edges of the front and back sides of each workpiece have slightly different shapes from each other. Thus, for accurate examination of such blanked workpieces, it is necessary to lay them on the conveyor belt so that the front sides of all the workpieces face the same direction. Also, even if the workpieces are laid with their front sides facing all up or all down, edge shapes also tend to change with time because the model is worn gradually. As the edge shapes change, light reflectance changes, thus affecting the accuracy of examination.

An object of the invention is to provide a device which can examine workpieces with high accuracy.

SUMMARY OF THE INVENTION

According to the invention, there is provided a device for examining flat workpieces having front and back sides, the device comprising a turntable having a workpiece-carrying portion formed from a transparent hard material, a conveyor for carrying the workpieces with front or back side thereof in contact with the conveyor surface, a transfer mechanism for moving the workpieces being carried on the conveyor onto the workpiece-carrying portion of the turntable, a guide for guiding the workpieces on the turntable to an examination point on the turntable while the turntable is turning, a camera for photographing the workpieces one by one when they reach the examination point, an image sensor unit for determining whether each of the workpieces photographed by the camera is defective or nondefective, and a workpiece discharge unit for discharging the defective and nondefective workpieces out of the turntable separately from each other, the image sensor unit including a lighting unit provided opposite the camera with the turntable therebetween for shedding light on each workpiece at the examination point through the turntable.

According to this invention, the lighting unit is a strobe operatively associated with the camera so as to flash when the camera is activated.

According to this invention, an oil film is formed between the workpieces and the turntable to prevent the workpieces from moving relative to the table.

According to this invention, a scraper for scraping off foreign matter or oil on the turntable is provided.

Works are examined on a turntable, not on the conveyor. Thus, any soiling, scratches or foreign matter on the conveyor will have no influence whatsoever on the accuracy of examination.

The transmission lighting arrangement allows the camera to clearly photograph works because works, which do not pass light, contrast clearly against the background, i.e. turntable, which is transparent and thus passes light, and because no reflected light enters the camera.

The hard turntable is practically scratch-free, and any soiling or foreign matter can be easily wiped off. Thus its surface can be kept clean for a long time.

The strobe lighting allows the camera to catch more vivid images of works.

Oil film formed on the surface of works serves as a kind of adhesive for keeping the works firmly stuck on the turntable. This makes it possible to turn the table at a higher speed and thus to examine a greater number of works per unit time.

Other features and objects of the present invention will become apparent from the following description made with reference to the accompanying drawings, in which:

DETAILED DESCRIPTION OF THE PREFERRED EMBODIMENT

Figure 1:
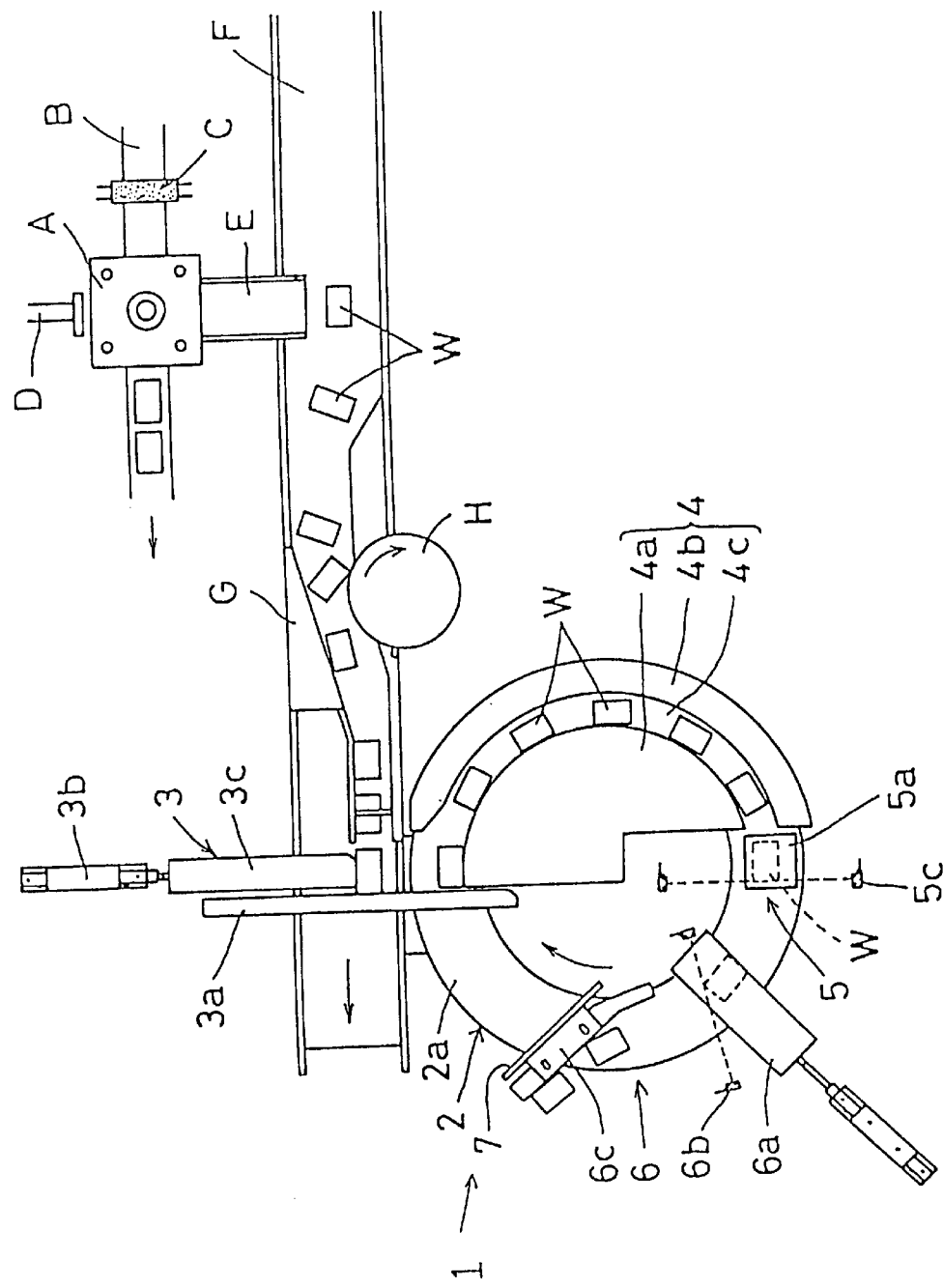
FIG. 1 is a plan view of an examination device embodying the present invention.

FIGS. 1 to 6 show an examination device embodying the present invention. The device 1 is mounted in a press line as shown in FIG. 1. The press line includes a press A for forming workpieces by blanking a sheet material B. The press has an oil application roller C for applying a small amount of oil to the sheet B.

Workpieces W are blanked from the sheet B by the press A while the sheet B is fed intermittently, and discharged through a chute E onto a belt conveyor F by a dispenser D.

The belt conveyor F may have a guide G for arranging the workpieces and a roller H for correcting the positions of workpieces.

The examination device 1 comprises a turntable 2 provided near the belt conveyor F, a pusher 3 for pushing workpieces W on the conveyor onto the turntable 2, a guide 4 for guiding workpieces W on the turntable 2 to an examination point, an image sensor 5 for distinguishing good workpieces from bad ones, a work discharge assembly 6 for discharging good workpieces and bad ones through separate discharge paths, and scrapers 7 for cleaning the work feeding surface of the turntable 2.

Figure 2:
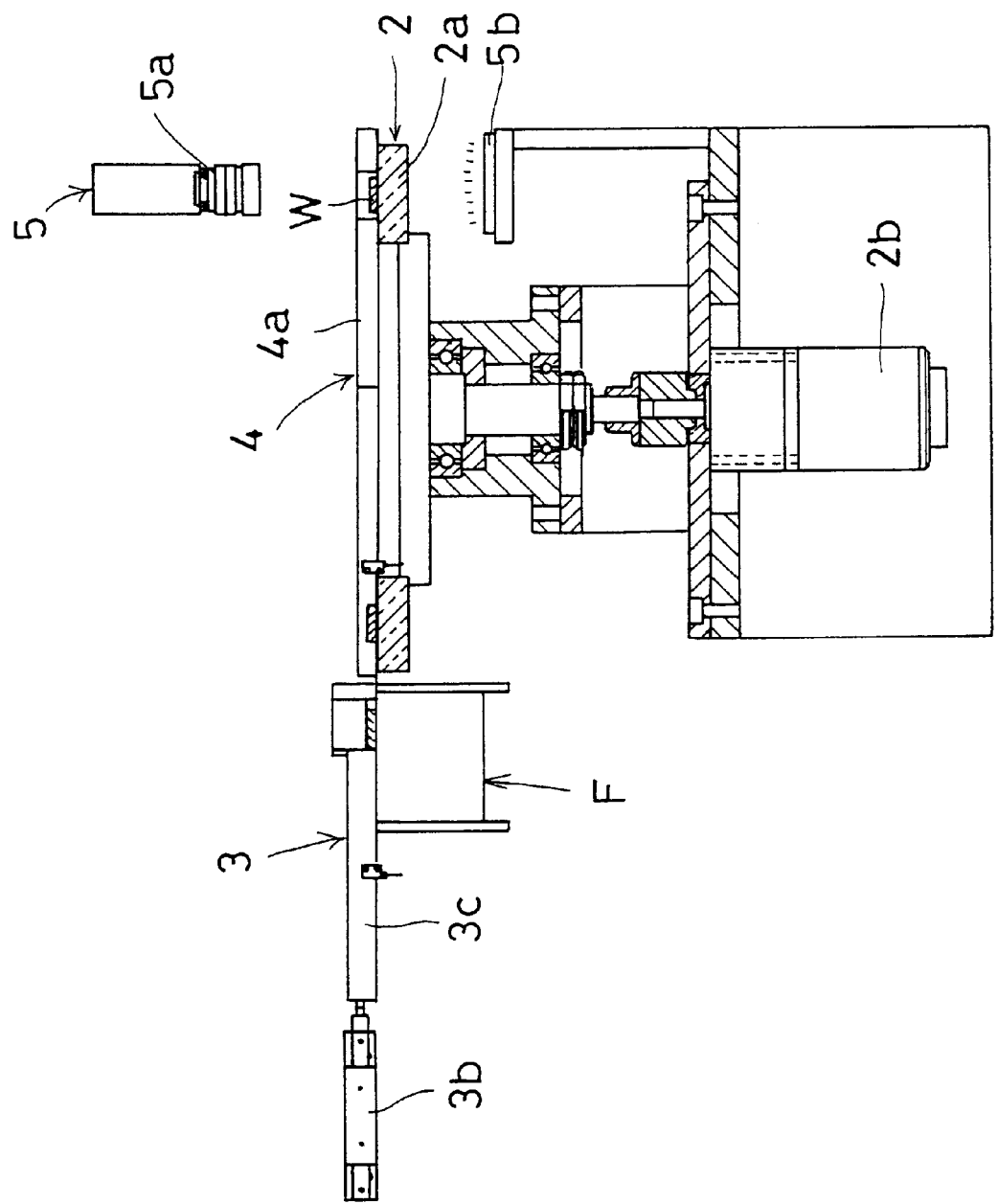
FIG. 2 is a vertical section of the same.
Figure 3:
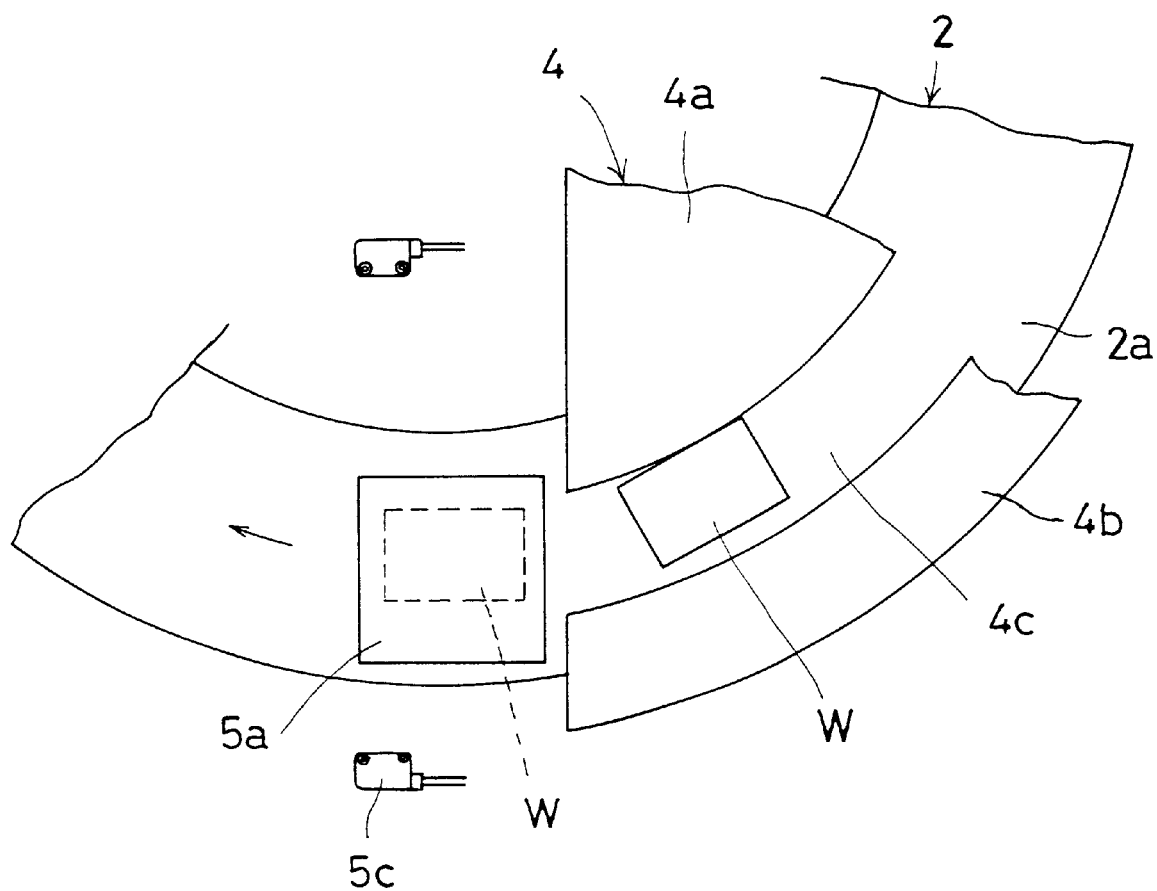
FIG. 3 is an enlarged plan view of a portion of the device of FIG. 1 where an image sensor is provided.
Figure 4:
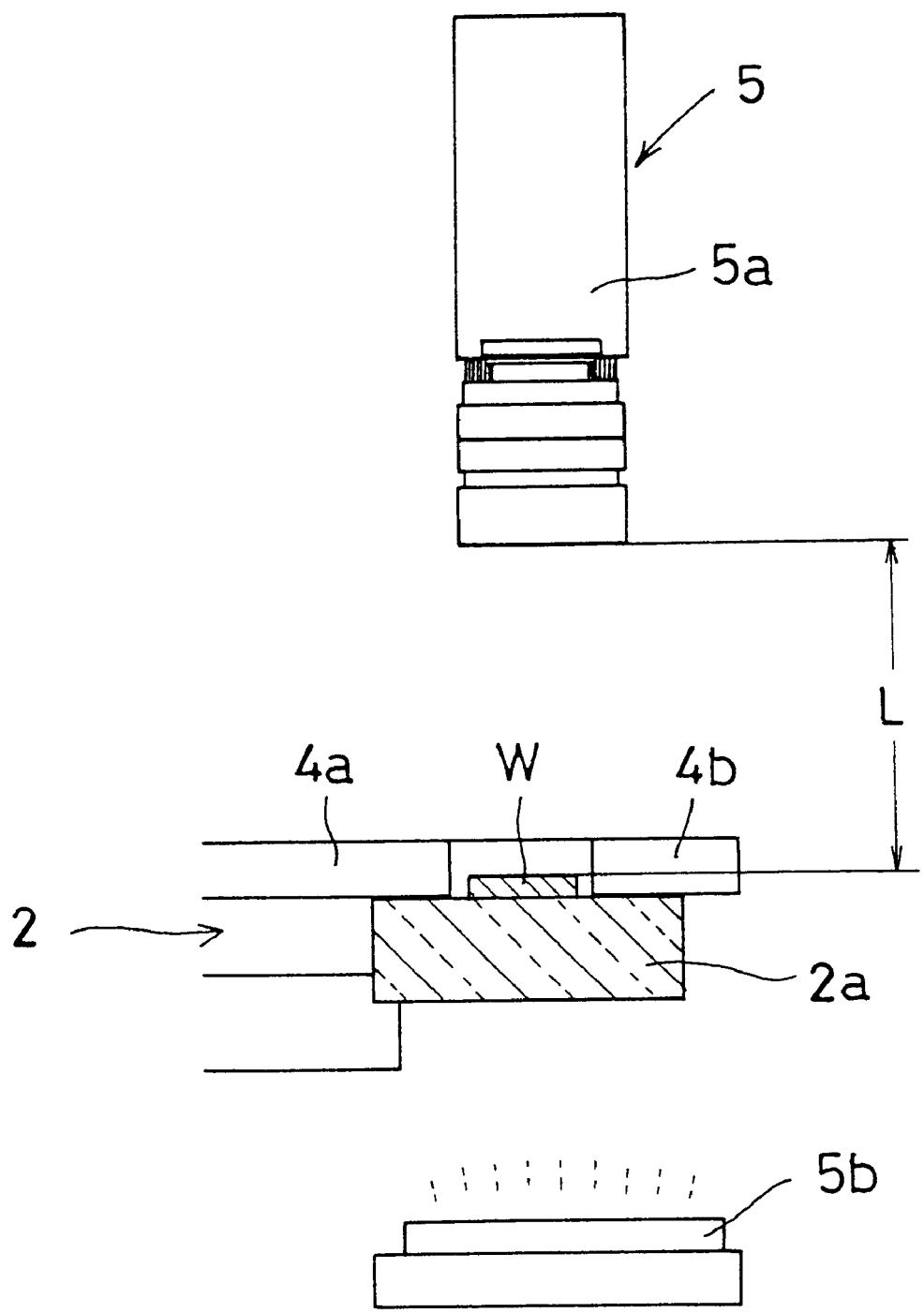
FIG. 4 is an enlarged sectional view of the portion.

The turntable 2 has its workpiece-carrying surface 2a formed from a transparent hard material (such as hard glass), and is continuously turned in the direction of the arrow in FIG. 1 by a motor 2b shown in FIG. 2.

The pusher 3 comprises an abutment plate 3a for stopping a workpiece being carried on the belt conveyor F, and a pushrod 3c reciprocated by an actuator 3b such as a hcylinder. When a sensor (not shown) detects that a workpiece has abutted the plate 3a, the pushrod 3c is advanced to move the workpiece W onto the turntable 2. But different means may be used to move workpieces onto the turntable.

The guide 4 comprises inner and outer guide frames 4a, 4b defining a workpiece feed path 4c therebetween. For smooth, efficient movement of workpieces on the table, the path 4c is preferably a circular path concentric with the turntable 2.

The image sensor 5 comprises a CCD camera 5a provided over the surface 2a of the turntable 2, a strobe 5b provided behind the table, opposite the camera, and a timing sensor 5c for actuating the camera when it detects that a workpiece has reached the examination point. A monitor may be added if required. The strobe 5b flashes simultaneously when the camera 5a is actuated.

If the guide frames 4a, 4b are in field of view of the camera together with a workpiece, it may be difficult to detect the edge of the workpiece. Thus, the image sensor 5 should be spaced from the outlet of the guide 4 so that the camera would not photograph the frames 4a, 4b.

The discharge assembly 6 comprises a discharge unit 6a for discharging good workpieces, a timing sensor 6b, and a discharge guide 6c for discharging defective workpieces.

When the timing sensor 6b detects a good workpiece, the discharge unit 6a is actuated to move the workpiece into a discharge path (not shown) for good workpieces. When the timing sensor detects a defective one, the discharge unit 6a remains deactivated. Thus the defective workpiece is guided by the discharge guide 6c and falls off the table.

The following are typical specs of the image sensor 5 used in the examination device: camera lens f=25 mm; horizontal field of view: 32 mm; horizontal resolution: 0.063 mm/dot (0.0063 mm/dot when the sub-pixel function is on); vertical field of view: 29 mm; vertical resolution: 0.128 mm/dot (0.0128 mm/dot when the sub-pixel function is on), distance L from the workpiece W to the camera 5a (FIG. 4): 120 mm.

Figure 6:
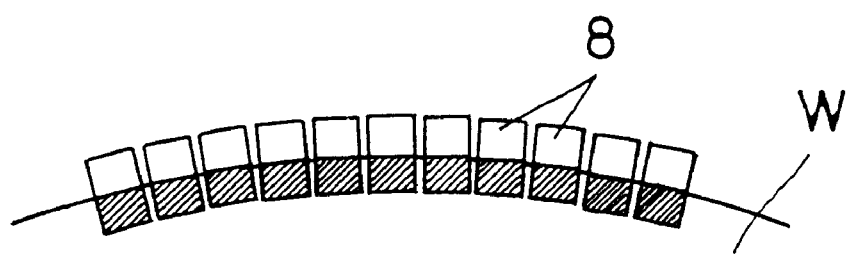
FIG. 6 shows how the image of an edge of a workpiece is divided into plural sub-sections to check the respective sub-sections separately from each other.

Any chipping along the edge of a workpiece is detected by dividing the edge into many sub-sections 8 as shown in FIG. 6, and checking each sub-section 8 by image density adjustment with the sub-pixel processing function activated.

The guide unit 4 makes the attitudes of workpieces W substantially uniform by the time they reach the examination point. But means may be provided for finely correcting the attitudes of workpieces at the examination point. The image sensor 5 can detect the amount of misalignment of slits or holes of workpieces and measure the inner and outer diameters of workpieces.

Figure 5:
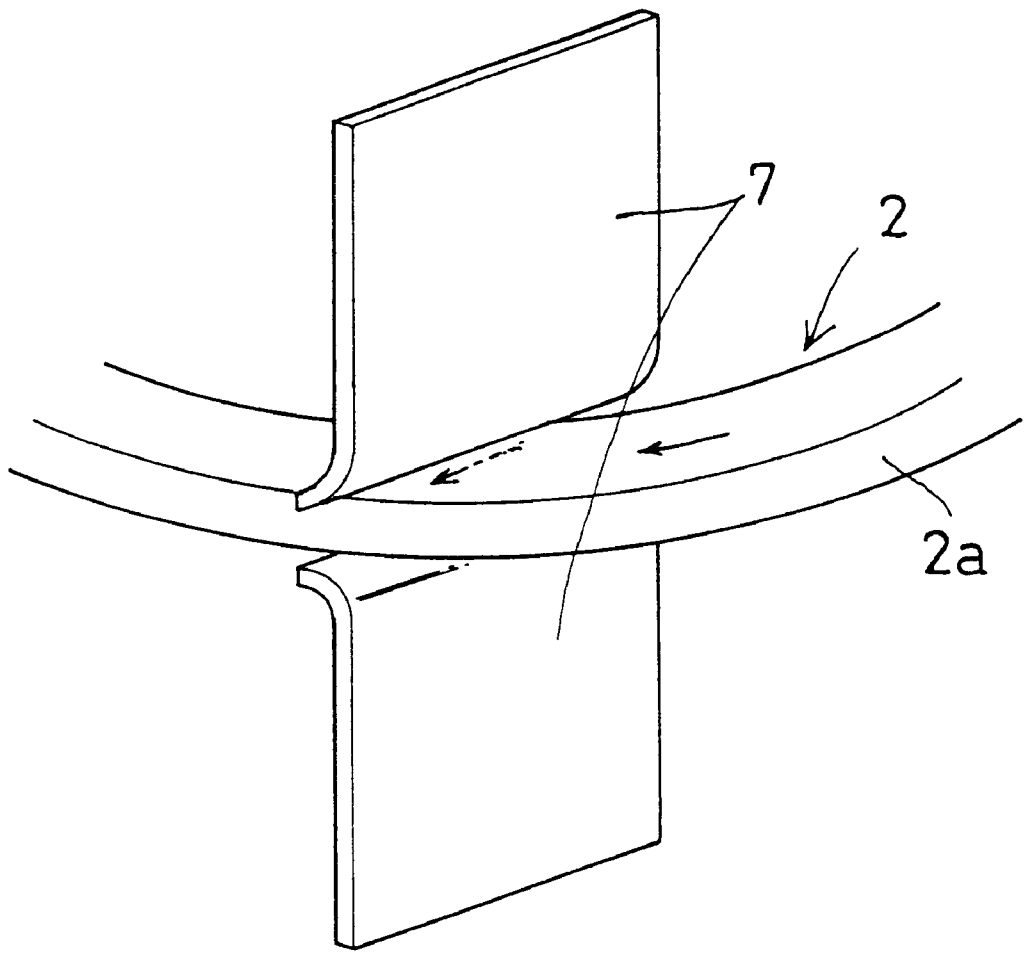
FIG. 5 is a perspective view showing how the scrapers are mounted.

As shown in FIG. 5, the scrapers 7 are rubber-made, and have their edges that are to be brought into contact with the table bent in a direction in which the table rotates. The scrapers 7 can scrape off any oil and foreign matter adhered to the surface 2a. Although the scrapers 7 cannot scrape off a thin oil film on the table surface, such a film will not appear in the camera image due to back lighting by the strobe.

The examination device 1 thus structured can examine the workpieces W on the turntable 2 for size and shape by means of the image sensor 5, thereby distinguishing good workpieces from defective ones.

This device 1 was used to check any chipping along the edges of coins (1-, 5-, 10-, 50-, 100-, 500-yen coins). To these coins, a small amount of oil was applied because coins tend to be contaminated with oil in a production line including a press.

It was found that the oil film formed on the coins worked like a binder to fix the coins to the table 2. Thus, even when the table was rotated at a speed of 30 meters per minute, it was possible to examine the coins with high accuracy because they never moved on the table.

For the actual accuracy of examination by the image sensor having the specifications mentioned above, due to external factors and the influence of the random-shutter camera, the minimum horizontal resolution was 0.0645 $mm^2$, and the maximum examination time per work (taking images, performing calculations and outputting the results) was about 60 ms. These figures are well above the standard.

If the table is rotated at a speed of 30 meters per minute with workpieces arranged thereon at intervals of 50 mm, it is possible to examine 600 workpieces per minute.

Applying oil to workpieces is desirable for two reasons, that is, 1) oil film serves as a kind of binder for fixing workpieces to the table, thereby preventing them from moving on the table, and 2) the oil serves as a kind of lubricant, thus preventing the surface of the table from being abraded or otherwise damaged by foreign matter when the table surface is brought into sliding contact with the scrapers. Thus, if no oil is applied to workpieces, it is recommended to apply oil on the table to cover the table surface with oil film.

Since workpieces are examined on the turntable, the surface condition of the conveyor has no influence on the accuracy of examination.

The transmission lighting system makes examination free from the problem of shape of sheared ends of the workpiece and makes it unnecessary to put blanked workpieces on the table so that their front sides will face the same direction. Since the turntable is made from a hard material and the cleaning scrapers are provided, the table surface is kept clean and damage-free. It is thus possible to maintain high accuracy of examination for a long time.

What is claimed is:

1. A device for examining flat workpieces having front and back sides, said device comprising a turntable having a transparent workpiece-carrying portion formed from a transparent hard material, a conveyor for carrying the workpieces with front or back side thereof in contact with the conveyor surface, a transfer mechanism for moving the workpieces being carried on said conveyor onto said workpiece-carrying portion of said turntable, a guide for guiding the workpieces on said turntable to an examination point on said turntable while said turntable is turning, a camera for photographing the workpieces one by one when they reach said examination point, an image sensor unit for determining whether each of the workpieces photographed by said camera is defective or nondefective, and a workpiece discharge unit for discharging the defective and non-defective workpieces out of said turntable separately from each other, said image sensor unit including a lighting unit, provided opposite said camera with said turntable between said camera and said lighting unit, operable to shed light through said transparent workpiece-carrying portion of said turntable on each workpiece at said examination point.

2. The device of claim 1 wherein said lighting unit is a strobe operatively associated with said camera so as to flash when said camera is activated.

3. The device of claim 1 wherein an oil film is formed between the workpieces and said turntable to prevent the workpieces from moving relative to said table.

4. The device of claim 3 further comprising a scraper for scraping off foreign matter or oil on said turntable.

5. The device of claim 2 wherein an oil film is formed between the workpieces and said turntable to prevent the workpieces from moving relative to said table.

* * * * *